United States Patent
Rupp

(10) Patent No.: US 6,821,786 B2
(45) Date of Patent: Nov. 23, 2004

(54) DIAGNOSTIC TEST FOR ELEMENTAL IMBALANCES

(75) Inventor: Michael E. Rupp, Redondo Beach, CA (US)

(73) Assignee: Future Data Inc., Redondo Beach, CA (US)

( * ) Notice: Subject to any disclaimer, the term of this patent is extended or adjusted under 35 U.S.C. 154(b) by 0 days.

(21) Appl. No.: 10/423,130

(22) Filed: Apr. 24, 2003

(65) Prior Publication Data

US 2003/0203495 A1 Oct. 30, 2003

Related U.S. Application Data

(60) Provisional application No. 60/375,566, filed on Apr. 25, 2002.

(51) Int. Cl.[7] ............................................. G01N 33/20
(52) U.S. Cl. ............................. 436/73; 422/56; 422/61; 436/74; 436/79; 436/80; 436/81; 436/82; 436/83; 436/84; 436/169
(58) Field of Search ........................... 436/73–74, 169, 436/79–84; 422/56–58, 61

(56) References Cited

U.S. PATENT DOCUMENTS

| | | | | |
|---|---|---|---|---|
| 3,006,735 A | * | 10/1961 | Jordan | 436/79 |
| 3,715,192 A | * | 2/1973 | Wenz et al. | 422/56 |
| 3,891,507 A | * | 6/1975 | Breuer | 435/14 |
| 3,964,871 A | * | 6/1976 | Hochstrasser | 435/10 |
| 4,094,647 A | * | 6/1978 | Deutsch et al. | |
| 4,166,719 A | * | 9/1979 | Renton | 436/84 |
| 4,275,031 A | * | 6/1981 | Fischer et al. | 422/57 |
| 4,388,271 A | * | 6/1983 | Kraemer et al. | 422/56 |
| 4,846,182 A | * | 7/1989 | Fogt et al. | 600/362 |
| 4,904,605 A | * | 2/1990 | O'Brien et al. | 436/169 |
| 5,071,623 A | * | 12/1991 | Akutsu | 422/56 |
| 5,178,831 A | * | 1/1993 | Sakota et al. | 422/56 |
| 5,403,551 A | * | 4/1995 | Galloway et al. | 422/58 |
| 5,710,372 A | * | 1/1998 | Becket | 73/53.01 |

FOREIGN PATENT DOCUMENTS

WO       00/46588     *   8/2000

OTHER PUBLICATIONS

Strain, W. H. et al, Nat. Bur. Stand. (U.S.), Spec. Publ. 1969, No. 312, 128–133.*
Selby, L. A. et al, Journal of the American Veterinary Medical Association 1970, 157, 1800–1808.*
Mills, C. F. Proceedings of the Nutrition Society 1974, 33, 267–274.*
Miller, W. J. Feedstuffs 1974, 46, 24–5, 35.*
Jackson, M. J. "Diagnosis and detection of deficiencies of micronutrients: mineral" British Medical Bulletin 1999, 55, 634–642.*

(List continued on next page.)

Primary Examiner—Arlen Soderquist
(74) Attorney, Agent, or Firm—Christie, Parker & Hale, LLP

(57) ABSTRACT

A self-diagnostic test, a self-diagnostic test apparatus, and method of manufacturing a self-diagnostic test for screening for elemental mineral imbalances in a patient utilizing an analysis of the reaction of mineral specific reagents to a sample from a patient are provided. In one embodiment, the invention is directed to a test for those elements that occur naturally in the body. In such an embodiment, the invention may test for those elements that comprise about 0.001% of the body weight or less (microtrace), those elements that comprise about 4% of the body weight or less (trace), those elements that comprise up to 96% of the body weight (mass), or any combination of the above.

31 Claims, 4 Drawing Sheets

OTHER PUBLICATIONS

Amelin, V. G. "Test method for the determination of overall quality characteristics of water using indicator papers" Journal of Analytical Chemistry (Translation of Zhurnal Analiticheskoi Khimii) 2000, 55, 480–485.*

Sandstrom, B, "Diagnosis of zinc deficiency and excess in individuals and populations" Food and Nutrition Bulletin, 2001 22, 133–137.*

Mertz W "The essential trace elements" Science, 1981, 213, 1332–8.*

Subramanian, K. S., et al, "Detection of trace metal deficiencies: Measurable parameters" Handbook of Metal–Ligand Interactions in Biological Fluids: Bioinorganic Medicine(1995, vol. 1, pp. 542–548, Editor(s): Berthon, Guy, Publisher: Dekker, New York.*

Hase, Y. et al, "Measurement of water quality with multiple reagent strips" Kogyo Yosui 1997, 469, 51–56.*

Salmenpera, L. "Detecting subclinical deficiency of essential trace elements in children with special reference to zinc and selenium" Clinical Biochemistry 1997, 30, 115–120.*

Tarjan, R. et al, Bibliotheca Nutritio et Dieta 1976, 23, 137–144.*

Suttle, N. F. Chemistry & Industry 1976, 559–962.*

Perez Melian . G, et al, Plant and Soil 1977, 48, 259–267.*

Mills, C. F. Philosophical Transactions of the Royal Society of London, Series B: Biological Sciences 1981, 294, 199–213.*

Spencer, K. et al, Journal of the Australian Institute of Agricultural Science 1982, 48, 101–103.*

Zhu, W. et al, Journal of Traditional Chinese Medicine 1983, 3, 145–150.*

Burns, I. G. et al, Communications in Soil Science and Plant Analysis 1984, 15, 1463–1480.*

Johansson, E. et al, Nuclear Instruments & Methods in Physics Research, Section B: Beam Interactions with Materials and Atoms 1987, B22, 179–183.*

Fell, G. S. et al, Current Topics in Nutrition and Disease 1988, vol. Date 1986, 18, 521–532.*

Szabo G et al, Orvosi Hetilap 1991, 132, 395–400.*

Wharton, B. A. Food Chemistry 1992, 43, 219–224.*

Ehmann, W. D. et al, Journal of Radioanalytical and Nuclear Chemistry 1993, 168, 223–231.*

Kawakubo K et al, Postgraduate Medical Journal 1994, 70, 215–219.*

Chappuis, P. et al, Trace Elem. Free Radicals Oxid. Dis., [Proc. Int. Congr. Trace Elem. Med. Biol.], 4th 1994, 46–56, Editor(s): Favier, A. E. et al, publisher: AOCS, Champaign, Ill.*

Delves, H. T. Special Publication—Royal Society of Chemistry 1995, 175, 27–38.*

Alfthan, G. et al, Journal of Trace Elements in Medicine and Biology 1996, 10, 77–87.*

Guth, H. J. et al, Trace Elements and Electrolytes 1997, 14, 154–158.*

Anonymous Journal of Trace Elements in Medicine and Biology 1997, 63.*

Lavon, R. et al, Journal of Plant Nutrition 1999, 22, 139–150.*

Kruse–Jarres, J. D. American Clinical Laboratory 2000, 19, 8, 10.*

Hoogenraad, Tjaard; "Wilson's Disease"; Major Problems In Neurology: Chapter 5 Clinical Manifestations; vol. 30; pp. 71–80.

Mason, Joel B.; "Consequences of Altered Micronutrient Status"; Cecil Textbook of Medicine; W.B Saunders Company; 21st Edition; vol. 2; pp. 1170–1178.

Garrison, Robert H. Jr., et. al."Trace Minerals: Chromium, Cobalt, Copper, Fluoride, Selenium, Zinc, and Other Minerals"; The Nutrition Desk Reference, Chapter 6; Keats Publishing; New Canaan, Connecticut; 3rd Edition; pp. 182–229.

Andersen S., et. al.;"Variations in Urinary Iodine Excretion and Thyroid Function. A 1–year Study in Healthy Men"; European J. of Endocrinology; 2001; vol. 144; pp. 461–465.

Biamonte, Michael; "Is Excess Copper the Hidden Cause of Your Health Problems?"; Health–Truth; http://www.health–truth.com/Articles/ChronicA/Chronic3.htm; Sep. 30, 2001.

"Cu++"; Proceedings of the Neurological Aspects of Wilson's Disease (NAWD Symposium; Sep. 2001; Bethesda, Maryland.

Allen, Jane E.; "How Do You Know If It's Attention Deficit/Hyperactivity Disorder?"; Los Angeles Times; May 8, 2000; Home Edition; Health Section; p. S–3.

Hall; Richard C., et. al.; "Physical Illness Manifesting as Psychiatric Disease"; Arch. Gen. Psychiatry; Sep. 1980; vol. 37; pp. 979–989.

Komaromy–Hiller, Gabor, et al.; "Comparison of Representative Ranges Based on U.S. Patient Population and Literature Reference Intervals for Urinary Trace Elements"; Clinica Chimica Acta.; (2000); vol. 296; pp. 71–90.

Paschal, Daniel C., et. al.; "Trace Metals in Urine of United States Residents: Reference Range Concentrations"; J. of Environmental Research, Section A.; (1998); vol. 76; pp 53–59.

Traub, Scott. J., Ed.; "Electrolytes, Other Minerals, and Trace Elements"; Basic Skills in Interpreting Laboratory Data, 2nd Ed.; (1996); pp. 115–120.

Kanabrocki, E.L., et. al.; "Circadian Variation in the Urinary Excretion of Electrolytes and Trace Elements in Men"; Am. J. of Anatomy; (1983); vol. 166; pp. 121–148.

Schuhmacher, M., et. al.; "Biological Monitoring of Metals and Organic Substances in Hazardous–Waste Incineration Workers"; Int. Arch. Occup. Environ. Health; Sep., 2002; vol. 75; No. 7; pp. 500–506.

Ichikawa; Y., et. al.; "Biological Monitoring of Cobalt Exposure, Based on Cobalt Concentration in Blood and Urine"; Int. Arc. Occup. Environ. Health; (1985); vol. 55; No. 4; pp. 269–276.

Fuortes, L., et. al.; "Marked Elevation of Urinary Zinc Levels and Pleural–Friction Rub in Metal Fume Fever"; Vet. Hum. Toxicol.; Jun., 2000; vol. 42; No. 3, pp. 164–165.

Giorgio; Anthony J., et. al.; "Determination of Urinary Copper By Means of Direct Extraction with Zinc Dibezyl Dithiocarbonate"; Am. J. of Clinical Pathology; Jan. 1964; vol. 11; No. 1; pp. 22–26.

Hauser, Russ, et. al.; "Urine Vanadium Concentration sin Workers Overhauling an Oil–Fired Boiler"; Am. J. of Industrial Medicine; (1998); vol. 33; pp. 55–60.

Nunnelley, L.L., et. al.; "Uremic Hyperstannum: Elevated Tissue Tin Levels Associated with Uremia"; J. Lab. Clin. Med.; Jan., 1978, vol. 91; No. 1; pp. 72–75.

"Heavy Metal Home Screen Kit for Personal Use"; http//www.chelationtherapyonline.com/technical/p72.htm; Target YourHealth.org.

Banta, Richard G., et. al.; "Elevated Manganese Levels Associated with Dementia and Extrapyramidal Signs"; J. Neurology; Mar. 1977; vol. 27; pp. 213–216.

* cited by examiner

DIAGNOSTIC TEST FOR ELEMENTAL IMBALANCES

CROSS-REFERENCE TO RELATED APPLICATION

This application is based on U.S. Application No. 60/375,566, filed on Apr. 25, 2002, the disclosure of which is incorporated by reference.

FIELD OF THE INVENTION

The present invention is generally related to a diagnostic test for detecting elemental imbalances, and more particularly to a diagnostic test for detecting imbalances in the set of elements that naturally occur in the human body.

BACKGROUND OF THE INVENTION

The medical community has long been aware that excessive levels of some naturally occurring minerals can lead to toxicity, which may express itself in a number of ways in the human body.

For example, excessive levels of heavy metals, such as lead, arsenic, mercury, cadmium, and chromium, may cause GI irritation, renal toxicity, cutaneous abnormalities, and central and peripheral nervous system toxicity. Other specific diseases and syndromes recognized by most medical directories as stemming from excessive mineral levels in the body include: chronic organic brain syndromes for aluminum; leishmaniasis for antimony; encephalopathy for arsenic; lung disease for barium and beryllium; periodontal diseases for bismuth; renal failure for cadmium; lung disease for chromium and cobalt; Wilson's disease and secondary cardiomyopathy for copper; idiopathic peripheral neuropathy for lead; manic, depressive, and bipolar disorders for lithium; specific toxicities for manganese and molybdenum; renal failure for mercury; lung disease and renal failure for nickel; renal failure for selenium; ataxia for thallium; specific toxicities for tin and titanium; and Crohn's disease for zinc.

Moreover, a number of recent studies indicate that a number of other mental and physical ailments can be correlated to simple nutritional imbalances. For example, studies indicate that attention deficit disorder (ADD), hyperactivity, and dyslexia may be the result of imbalances in calcium, magnesium, iodine, iron and zinc. In addition, excessive concentrations of copper, lead, cadmium, and aluminum have been seen in learning disabled children. (A. Buresz, "Attention Deficit Disorder & Hyperactivity Success", http://www.all-natural.com/add.html.)

A recent study of autism patients at the Pfeiffer Treatment Center showed that nearly all of the institute's autistic patients exhibited a metal metabolism disorder indicated by elevated copper levels. ("Protocol for Autism Spectrum Disorders", http://www.hriptc.org/autism-protocol.html.)

Researchers at Massachusetts General Hospital have found that a buildup of copper and zinc in the brain causes protein deposits that are a hallmark of Alzheimer's disease. (S. Hensley, "Study Says Buildup of Copper, Zinc May be Cause of Alzheimer's Disease", The Wall Street Journal, Jun. 21, 2001.)

Recent studies have also indicated a link between mercury poisoning from vaccines containing the preservative thimerosal and autism in children. (M. C. Fisk, "Mercury's Legal Morass", The National Law Journal, Mar. 18, 2002.)

Despite the substantial evidence for a link between mineral imbalances in the body and a host of physical and psychological illnesses, currently most mineral screening tests only look for excessive concentrations of three heavy metals: mercury, lead and arsenic. Further, most of the screening tests that are currently administered generally require the use of blood serum and an in-house laboratory analysis. Both of these requirements necessitate that the patient visits a medical clinic and that the test be administered by a trained medical professional raising the cost of screening significantly.

Accordingly, a need exists for a test capable of accurately diagnosing an imbalance in an elemental mineral that can be both administered and analyzed at home by a patient.

SUMMARY OF THE INVENTION

This invention is directed to a self-diagnostic test for screening for elemental mineral imbalances in a patient utilizing an analysis of the reaction of mineral specific reagents to a sample from a patient. The test may be designed to monitor any and all of the elements of the periodic table.

In one embodiment, the invention is directed to a test for those elements that occur naturally in the body. In such an embodiment, the invention may test for those elements that comprise about 0.001% of the body weight or less (microtrace), those elements that comprise about 4% of the body weight or less (trace), or those elements that comprise up to 96% of the body weight (mass).

In another embodiment, the invention is directed to a test for those elements that do not occur naturally in the body.

In still another embodiment, the invention is directed to a test for those elements that are indicative of a specific disorder of the body, such as a combination copper/zinc analysis for Wilson's disease.

In yet another embodiment, the invention is directed to a test that can be analyzed visually, such as through colorimetric analysis.

In still yet another embodiment, the invention is directed to a test capable of measuring mineral imbalances in a patient's urine.

In still yet another embodiment, the invention is directed to a method of manufacturing a mineral self-diagnostic test.

In still yet another embodiment, the invention is directed to an apparatus for administering a mineral self-diagnostic test.

BRIEF DESCRIPTION OF THE DRAWINGS

These and other features and advantages of the present invention will be better understood by reference to the following detailed description when considered in conjunction with the accompanying drawings, wherein.

DETAILED DESCRIPTION OF THE INVENTION

This present invention is directed to a self-diagnostic test kit for screening for elemental mineral imbalances in a patient, referred to as the diagnostic test herein.

Figure 1:
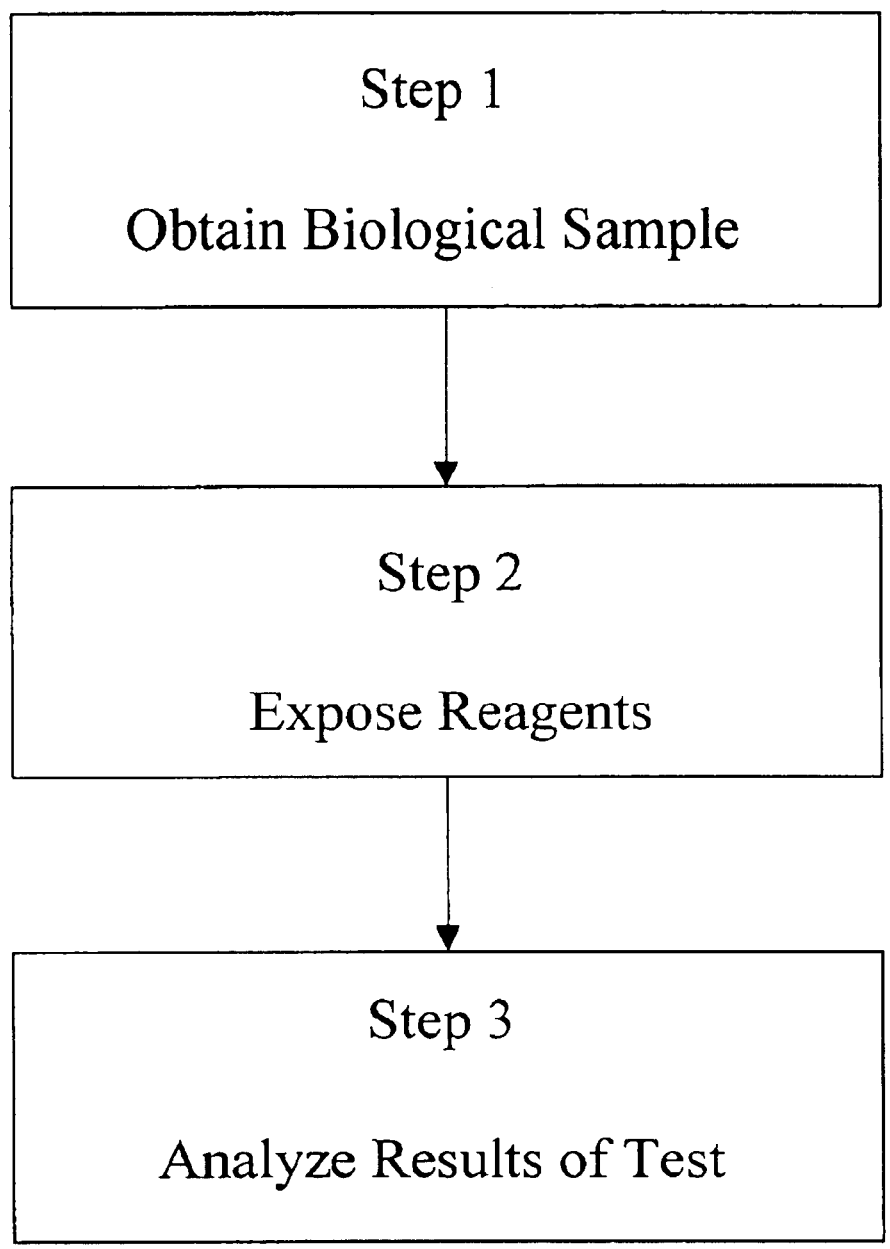
FIG. 1 is a flow chart of a method of testing a patient for mineral imbalances according to the current invention.

FIG. 1 shows a flow chart of a method for diagnosing a mineral imbalance in a patient utilizing the test according to the current invention. As shown, in step 1 a sample is obtained from the patient. Although any specimen containing sufficient and suitable biological material for testing with a reagent may be utilized, in one embodiment the sample is a waste product such as urine. It should be understood, however, that the biological sample may also include other suitable materials such as blood, saliva, mucous, tears, etc.

In step 2 the biological sample is applied to the reagents selected for the analysis of a particular mineral or set of minerals. Any suitable reagent may be utilized such that the reagent is capable of detecting specified levels of a mineral in the biological sample. A list of suitable reagents for a number of exemplary minerals is provided in Table 1, below.

TABLE 1

Mineral Reagents

| Element | Suitable Reagents |
|---|---|
| Aluminum | lumogallion; o,o'-dihydroxyazobenzene; aluminon; oxine |
| Antimony | 5-Br-PADAP; rhodamine B; brilliant green; thionalide |
| Arsenic | arsemate; thionalide; nitrocatechol; ethyl violet |
| Barium | dimethylsulfonazo-III; sulfonazo-III; chlorophosphonazo-III |
| Beryllium | chromazural S; arsenazo-I; acetylacetone; beryllon-III; 2-methyloxine; aluminon |
| Bismuth | bismuthio-II; XO; 5-Br-PADAP; DDTC; dithizone |
| Boron | azomethine-H; chromotropic acid; dinitronaphthalenediol; 3,5-di-t-butylcatechol; 2,6-dihydroxybenzoic acid; curcumin |
| Bromine | bindschedler's green leuco base; diphenylcarbazone |
| Cadmium | GHA; PAN; DDTC; cadion; dithizone; 5-Br-PADAP; 5-Br-DMPAP |
| Calcium | PC; MX; indo 1; indo 1-AM; chlorophosphonazo-III; neo-thorin; fluo 3; fluo 3-AM; arsenazo-III; HDOPP-Ca; rhod 2; rhod 2-AM; GHA; quin 2; quin 2-AM; calmagite; fura 2; fura 2-AM |
| Cerium | PAN; formaldoxime; pyrogallol red |
| Cesium | cesibor; tetraphenylborate |
| Chlorine | thio-michler's ketone; MQAE; SPQ; diethylcarbamate-Cu; diphenylcarbazone; triocytlin; tris(1,10-phenanthroline)Fe(II) |
| Chromium | 5-Br-PAPS; o-nitrophenylfluorone; diphenylcarbazide; 5-Br-PADAP |
| Cobalt | BTAMB; TAMSMB; 5-Cl-PADAB; dithizone; 3,5-diBr-PAMB; nitroso-DMAP; 5-Br-PADAP; nitroso-PSAP; nitroso-DEAP; 5-Br-PADAB |
| Copper | bathocuproin disulfonic acid disodium salt; bathocuproin; TAMSMB; 3,5-diBr-PAESA; sodium bicinchoninate; neocuproin; 5-Br-PSAA; BTAMB; TMPyP; Na-DDTC; dithizone |
| Europium | $EuAc_3$; $Eu_2O_3$ |
| Fluorine | alfusone; chromazurol S |
| Gadolinium | $GdAc_3$; $Gd(NO_3)_2$ |
| Gallium | lumogallion; sincon; oxine; rhodamine B; semiethylxylenol Blue |
| Germanium | phenylfluorone |
| Gold | $KAu(CN)_2$; $NaAuCl_4$; $KAuCl_4$; $KAuI_4$; rhodamine B; 5-(p-dimethylaminobenzylidene)rhodamine |
| Indium | PAN; PAR; oxine; dithizone |
| Iodine | $K_2HgI_4/I_2$; bindschedler's green leuco base; diphenylcarbazone; tris(1,10-phenanthroline)Fe(II) complex |
| Iridium | $K_3IrCl_6$; $Na_3IrCl_6$; $SnCl_2$-HBr; leuco-crystal violet |
| Iron | bathophenanthroline disulfonic acid disodium salt; bathophenanthroline; nitroso-PSAP; TPTZ; PDTS; PDT; nitro-PAPS; 3,5-diBr-PAMB; 5-Br-PSAA; PPKO; ferrene S; oxine |
| Lead | $PbAc_2$; $PbCl_2$; $Pb(NO_3)_2$; MePbAc; TPPS; PAR; dithizone; DDTC |
| Lithium | thorin; bibenzyl-14-crown-4; phosphododecyl-14-crown4; TTD-14-crown-4; methyldodecyl-12-crown-4; dibenzothiazolylmethane; oxine |

TABLE 1-continued

Mineral Reagents

| Element | Suitable Reagents |
|---|---|
| Manganese | PAN; TAR; 1,10-phenanthroline; 2-methyloxine |
| Mercury | $EtHgCl_2$; EtHgphosphate; $Hg(CN)_2$; EtHgthiosalicylate (thiomersal); mersalyl; PCMB; PHMB; PCMBS; PhHgAc; $HgCl_2$; $HgAc_2$; $HgSO_4$; mercurochrome; Baker's reagent (2Hg); tetrakismercuryacetate (TAM)(4Hg); STTA; dithizone; thio-Michler's ketone; di-alpha-napthaylthiocarbonate |
| Molybdenum | PAR; oxine; DDTC; toluene-3,4-dithiol |
| Nickel | TAMSMB; BTAMB; PAN; 3,5-diBr-PAMB; dimethylglyoxime; 5-Br-PADAP |
| Niobium | PAR; sulfochlorophenol-S; TPAC; XO; BPR; oxine; phenylfluorone |
| Nitrogen | kalibor; phenol; pyradine-pyrazolone; o-phthalaldehyde; 4-aminonahthalene-1-sulfonate; 4-hydroxyxoumarine; chromotropic acid; m-phenylenediamine |
| Osmium | $Os(NH_3)_6I_3$; $K_2OsCl_6$; $K_2OsO_4$; bismuthio-II; tiron; PAR; TPAC; brilliant green |
| Paladium | $K_2PdCl_4$; $K_2PdBr_4$; $K_2PdI_4$; $PdCl_2$; $Pd(NO_3)_2$; BTAMB; 5-Br-PSAA; 5-Br-PAPS; thiooxine; 5-Br-PADAP; rhodamine B; p-nitroso-N, N'dimethylaniline; thio-Michler's ketone |
| Phosphorus | Co(3)-5-Cl-PADAP; malachite green |
| Platinum | $K_2PtCl_4$; $K_2PtCl_6$; $K_2PtI_6$; $K_2Pt(NO_2)_4$; $Pt(NH_3)_2Cl_2$; $Pt(ethylenediamine)Cl_2$; $K_2Pt(CN)_4$; 5-Br-PAPS; dithizone; p-nitroso-N,N'-dimethylaniline |
| Potassium | kalibor; bis(benzo-15-crown-5); 4TF; 6TF; picrylaminocrown; picrate; picrylamine; benzo-18-crown-6 |
| Rhenium | $ReCl_3$; 2-furildioxime; dimethylglyoxime; methylene blue |
| Rhodium | 5-Br-PAPS; oxine; p-nitroso-N,N'dimethylaniline |
| Rubidium | kalibor |
| Ruthenium | TPTZ; oxine; 1,10-phenanthroline; 5-Br-PAPS |
| Samarium | $SmAc_3$; $Sm(NO_3)_3$; $SmCl_4$ |
| Scandium | chlorophosphonazo-III; PAN; BPR; 5,7-dichloro-oxine; quinizarin |
| Selenium | bismuthiol-2; 2,3-diaminonaphthalene; 3,3-diaminobenzidine; o-phenylenediamine; 4-chloro-o-phenylenediamine |
| Silicon | ammonium molybdate; malachite green |
| Silver | $AgNO_3$; $KAgCN_2$; 3,5-diBr-PADAP; 3,5-diBr-PAESA; 5-(p-dimethylaminobenzylidene rhodamine; 2-amino-6-methylthio-4-pyrimidine-carboxylic acid |
| Sodium | bis(12-crown-4); nitrophenylazo-15-crown-5; oxine |
| Strontium | PC; sulfonazo-III; dinitrosulfonazo-III; murexide |
| Sulfur | pararosaniline; barium chloranilate; methylene blue; O-phthalaldehyde; p-phenylenediamine; tris [2-(phenyliminomethyl)pyridinato]iron; 2-aminoperimidine HCl/HBr; |
| Tellurium | bismuthiol-2; diethydithiocarbamate |
| Thallium | rhodamine B; malachite green; dithizone |
| Thorium | $Th(NO_3)_4$; arsenazo-III; thorin; 5-Br-PADAP; morin |
| Tin | PV; SATP; toluene-3,4-dithiol; oxine; phenylfluorone |
| Titanium | diantipyrylmethane; tiron; BPR; 0,0'-dihydroxyazobenzene; crystal violet; alizarin |
| Tungsten | $Na_2WO_4$; toluene-3,4-dithiol; oxine |
| Uranium | $UO_2Ac_2$; $K_3UO_2F_5$; $UO_2(NO_3)_2$; $UO_2SO_4$; arsenazo-III; PAN; 5-Br-PADAP; oxine |
| Vanadium | PAR; BPA; 5-Br-PAPS; oxine; 3,5-diBr-PADAP; 3,5-diBr-PAMB; 5-Br-PADAP |
| Ytterbium | $TbCl_3$; $YbAc_3$ |
| Zinc | zincon; 5-Br-PAPS; PAN; XO; TMPyP; zinquin ethyl ester; dithizone; T(5-St)P |
| Zirconium | $Zr(NO_3)_4$; arsenazo-III; PV; TAN; XO; 5-Br-PADAP; morin; alizarin red S |

Although exemplary reagents for most minerals are listed above, it should be understood that any reagent suitable for a visual detection of a particular concentration of a particular element may be utilized in the current invention. Moreover, although specific elements are listed above, it should be understood that any combination of elemental reagents could be used to create a diagnostic test according to the current invention.

Returning to FIG. 1, in step 3 the exposed reagents are compared to a standard for analysis and the results read. Such analysis may take the form of any suitable system of measuring the reaction of a reagent to a particular element. For example, in a visual indicating reagent, such as those listed in Table 1, above, any standard method of visual interpretation may be utilized, such as, a simple colorimetric analysis or a Patterson interpretation.

Figure 2:
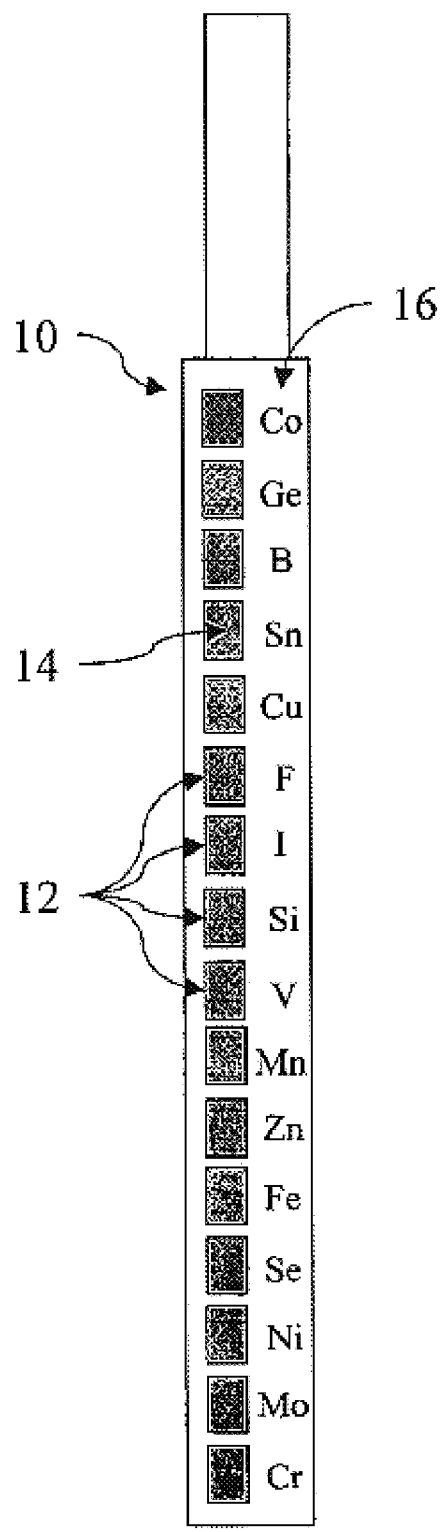
FIG. 2 is a schematic view of a diagnostic test according to the invention.

FIG. 2, shows a schematic of an exemplary embodiment of a diagnostic test according to the current invention. The diagnostic test generally comprises a body 10 having a multiplicity of regions 12 of reagents disposed thereon. The test further comprises an indicator portion 14, and a scale 16 designed to indicate which elemental mineral is being measured by each of the reagent regions 12.

The body 10 of the diagnostic test may be made of any material suitable for containing and separating the reagent regions 12. Preferably the body of the test is made from a material that is unreactive toward the reagents utilized. For example, the body 10 may be made of a plastic, a non-reactive metal, or a paper product, etc. Further, although the body is shown here as a rectangular dipstick, the body can take any shape suitable for conducting the diagnostic test.

Likewise, the reagent regions 12 and indicator portions 14 may comprise any construction suitable for containing the reagent material. For example, the reagents could be kept as liquids in reagent wells on the body of the test. In one exemplary embodiment, the reagents are absorbed and then dried onto a portion of a web of porous material, such as paper or cloth, such that a single substrate, suitably divided may be utilized to hold all of the reagent materials. Again, although the reagent regions and indicator portions are arranged linearly in two columns in the embodiment shown in FIG. 2, it should be understood that any arrangement of reagents may be utilized such that the reagents do not interact during testing, and such that a positive indication can be read.

Finally, although the scale 16 utilized in the embodiment shown in FIG. 2 is printed onto the body 10 of the test and allows analysis of all of the reagents simultaneously, it should be understood that the scale may comprise any device suitable for providing the user a system for indicating a positive test. For example, the scale may be provided on a separate structure which may be slipped over or laid next to the test. Alternatively, the scale may be a manual or color scale which allows comparison of the indicator portion with a standard. Likewise, the actual method of analysis is only dependent on the nature of the reagents utilized for the test. For example, if all of the reagents utilized indicate via a visible reaction or color change, a visual or colorimetric analysis of the results of the test may be employed. Alternatively, a separate handheld electronic device such as a chromatograph, pH meter, etc, may be provided to the user along with the test for analysis of the results.

Regardless of the actual physical design of the analyzer, it should be understood that in all cases the reagent is chosen and deposited such that it reacts to a specific concentration of a particular element. For example, the concentration of the reagent itself may be modified so that it only reacts with the corresponding mineral at a specific concentration. The sensitivity of the reagent may be modified by any suitable means, such as by diluting the reagent so that a visible reaction only occurs at sufficiently high concentrations of the element. Such concentrations are preferably set using the correct balanced concentration of the specified element within the body. For example, appropriate fasting concentrations of some specific exemplary minerals in the human body as suggested by the Food and Drug Administration are listed below in Table 2. It should be understood that the levels provided are only exemplary and that concentration levels of other mineral elements are well-known to those in the medical community.

TABLE 2

Levels of Elemental Minerals in Healthy Patients

| Element | Concentration |
|---|---|
| As | 2–3 mcg/L |
| Ca | 2.2–2.6 mM |
| Cr | 1–9.6 nM |
| Cu | 11–24 μM |
| I | 7.8 nM |
| K | 3.5–5.0 mM |
| Mg | .1–1.1 mM |
| Na | 136–145 mM |
| P | 0.8–1.5 mM |
| Pb | <0.5 μM |
| Se | 1–3.2 μM |
| Zn | 11–24 μM |

Accordingly, using these levels a test is devised either for excessive mineral imbalances or deficient mineral imbalances. It should be understood that in either case the reagent should be provided in a concentration sufficient to detect the desired level of mineral. For example, using the values from Table 2, a test looking for an excessive level of Zn can be designed such that the appropriate reagent only produces a reaction where the concentration of Zn in the biological sample rises above the 24 μM level. Alternatively a test looking for deficient levels of Zn can be designed such that the appropriate reagent only produces a reaction if the concentration of Zn in the biological sample is at least 11 μM. In such a test, a diagnosis would be made by observing those reagents which do not visibly react.

The exemplary test, shown in FIG. 2 is for diagnosing imbalances, such as excesses, in micro trace elements, i.e., those elements which comprise about 0.001% of a healthy person's standard body weight or less (B, Ge, F, I, Si, V, Cr, Co, Cu, Fe, Ni, Mo, Se, Zn, Sn, and Mn) and it shows those reagents which are designed to indicate for those micro-trace elements (dithizone, phenylfluorone, azomethane, oxine, alfusone, bindschedler's green, malachite green, PAN, bismuthiol-2, and 5-Br-PAPS). It should be understood that this combination of elements and reagents is only provided as an example and that any combination of reagents may be utilized to provide a diagnostic test customized for a particular screening. Further, even with regard to this specific test for the "micro-trace" elements it will be understood that the selection of reagents is only dependent on the nature of test. In the exemplary test shown in FIG. 2, several reagents that are sensitive to multiple elemental minerals are utilized. Although this choice of reagents reduces the cost of the test, it will be understood that additional clinical testing would be required to determine the absolute identity of an unbalanced elemental mineral. Alternatively, reagents with more specificity, i.e., that react only with one of the chosen elemental minerals, could be chosen such that a more detailed analysis of the identity of the unbalanced elemental minerals could be determined.

In another example, the test may diagnose imbalances in the trace elemental minerals that occur in the body, i.e., those elements that comprise at least about 4% of a healthy person's body weight (Ca, Cl, Mg, P, Na, and S). The reagents used in such a test may include: PC, MQAE; malachite green, oxine, and methylene blue.

In still another example, the diagnostic test might monitor the balance of the mass elements in the body, i.e., those elements which, in combination, make up at least 96% of a healthy person's body weight (C, N, 0 and H). The reagents used in such a test may include: kalibor; phenol; pyradine-pyrazolone; o-phthalaldehyde; and 4-aminonaphthalene-1-sulfonate.

In yet another example, the diagnostic test might monitor all naturally occurring elemental minerals which do not occur naturally in the body. Such a test would include reagents for: Li, Be, Ne, Al, Sc, Ti, Ga, As, Br, Kr, Rh, Sr, Y, Zr, Nb, Tc, Ru, Rh, Pd, Ag, Cd, In, Sb, Te, Xe, Cs, Ba, La, Hf, Ta, W, Re, Os, Ir, Pt, Au, Hg, Ti, Pb, Bi, Po, At, Rn, Fr, Ra, Ac, Ce, Pr, Nd, Pm, Sm, Eu, Gd, Tb, Dy, Ho, Er, Yb, Lu, Th, Pa and U. The reagents used in such a test may include: oxine, aluminon, PAN, alizarin, arsemate, bindschedler's green leuco base, PC, 5-Br-PADAP, rhodamine-B, diBr-PADAP, dithizone, brilliant green, bismuthiol-2, cesibor, sulfonazo-III, methylene blue, and leuco-crystal violet, etc.

Finally, yet another exemplary test may monitor the presence of man-made elements in the body. Such elements include: Np, Pu, Am, Cm, Bk, Cf, Es, Fm, Md, No, La, Rf, Db, Sg, and Bh. Although many of these elements are unstable, the presence of any of the elements would be considerably toxic.

Alternatively, the test may be designed such that it monitors for specific combinations of elements, which are indicative of particular illnesses. Examples of illnesses and the excessive mineral imbalances correlated therewith are provided in Table 3, below.

TABLE 3

Correlation of Diseases with Excessive Elemental Imbalances

| Disease | Elements |
| --- | --- |
| ADD/ADHD | B, Cu, Cd, Hg, Mn |
| Alzheimer's Disease | Al, Cu, Fe |
| Anemia | Zn |
| Ataxia | Tl, Hg |
| Bipolar Disorder | Li |
| Birth Defects | Co, I, Mn, Se, Zn, Hg, V |
| Blood Disorders | As, Th |
| Brain Damage | Mn, Hg |
| Brain Disease | Ba, Al |
| Breast Cancer | Ra, U |
| Breathing Disorders | B, Cr, Co, Cu, Ni, Al, Sb, Ag, V |
| Bone Cancer | Ra, Pu, U, Bi |
| Cardiomyopathy | Cu |
| General Cancer | Cr, F, Ra |
| Crohn's Disease | Zn |
| Depressive Disorders | Li |
| Gen. Bone Disorders | Pb, P, F |
| Encephalopathy | As |
| Eye Damage | Sb, Hg |
| Heart Damage | P, Sb |
| High Blood Pressure | Ba |
| Infertility | F, Se, Pb |
| Intestinal Disorders | Sb, Zn, Co, Cu, Cd, Sn, Zn, Hg, Tl |
| Leishmaniasis | Sb |
| Liver Cancer | Ra, Pu, U |

TABLE 3-continued

Correlation of Diseases with Excessive Elemental Imbalances

| Disease | Elements |
| --- | --- |
| Liver Damage | Cu, P, Mn, Sn |
| Lung Damage | Cd, P, F, Sb, Hg |
| Lung Disease | Be, Pu, Cu, Ni, Co |
| Lung Cancer | Ni, Rn, Th |
| Kidney Damage | Cu, P, Mn, Sn, Pb, Hg |
| Kidney Disease | U, Cr, Cd |
| Manic Disorders | Li |
| Nerve Damage | Se, Pb, Hg, Tl |
| Neuropathy | Pb |
| Organ Damage | Ba, Cr |
| Pancreatic Cancer | Th |
| Periodontal Disease | Bi |
| Psychosis | As, Hg |
| Renal Failure | Cu, Hg, Ni, Se, Zn |
| Retardation | I, Zn, Hg |
| Skin Disorders | Hg, As, Cr, Cu, Se, Sb, Ag |
| Wilson's Disease | Cu |

In addition to the above diseases, which are potentially caused by excessive concentrations of elemental minerals in the body, the diagnostic test could be designed such that it detects mineral deficiencies in the body. As discussed above, such a test could be designed with reagents in such a concentration or of such a design that they do not indicate when an inadequate level of a mineral element is found in the body. Accordingly, a reading of such a test would show the user those minerals whose intake should be increased.

Tests for elemental deficiencies may be designed identically to the tests discussed above. In addition, the test may be divided into the naturally occurring, micro-trace, trace, mass, and man-made categories described above. Alternatively, tests may be designed as above to diagnose specific illnesses related to mineral deficiencies. Examples of diseases related to deficiencies in particular elemental minerals are provided in Table 4, below.

TABLE 4

Correlation of Elemental Deficiencies with Disease

| Element | Diseases |
| --- | --- |
| B | arthritis, memory loss, bone loss, muscle pain, Carpal Tunnel Syndrome, osteoperosis, receding gums, infertility |
| Ca | acne, cancer, arthritis, cavities, acidosis, cataracts, ADD, asthma, fibromylagia, Bell's palsy, gallstones, cramps, high cholesterol, Carpal Tunnel Syndrome, chronic fatigue syndrome |
| Cr | anxiety, hyperinsulinism, ADD, hypoglycemia, hyperactivity, arteriorsclerosis, bipolar disease, manic depressive illness, infertility, obesity, depression, diabetes, neuropathy, high blood cholesterol |
| Co | digestive disorders, anemia, fatigue, nerve damage, myelin sheath damage, Multiple Sclerosis |
| Cu | allergies, Kawasaki disease, anemia, liver cirrhosis, aneurysm, osteoporosis, arthritis, parasites, edema, Parkinson's disease, hernias, ruptured disc, high blood cholesterol, skin eruptions, hyper thyroid, hair loss, heart disease, schizophrenia |
| Ge | asthma, leukemia, breast cancer, lung cancer, bladder cancer, neuralgia, nephritis, hypertension, neurotic disorders, hepatic cirrhosis |
| Au | arthritis, gland dysfunction, brain dysfunction, heat flashes, chills, cancer, insomnia, circulatory disorders, depression, obesity, digestive disorders, SAD, addiction, |
| I | acne, hyper thyroidism, cretinism, lethargy, depression, miscarriage, goiter, sterility, infertility |
| Fe | anemia, fatigue, anorexia, growth retardation, constipation, dizziness, headaches, depression, dysphasia, |
| Li | alcoholism, bi-polar, manic depression |

TABLE 4-continued

Correlation of Elemental Deficiencies with Disease

| Element | Diseases |
|---|---|
| Mg | asthma, anorexia, migraines, cramps, convulsions, tremors, myocardial infarction, depression, vertigo, kidney stones |
| Mn | carpal tunnel syndrome, multiple sclerosis, nerve problems, deafness, gout, infertility, tinnitus, tremors, miscarriage |
| Mo | acne, eczema, Epstein Barr, anemia, gout, asthma, Bell's palsy, impotency, insomnia, cancer, cirrhosis, candidiasis, lupus, lyme disease, multiple sclerosis, obesity, depression, diabetes, |
| Pt | cancer, nerve damage, chronic fatigue, neuralgia, gland dysfunction, insomnia |
| K | poor circulation, insomnia, intestinal pain, chronic fatigue syndrome, diabetes, earaches, edema, prolapsed uterus, swollen glands, tissue anemia, hypertension |
| Se | liver spots, immune deficiencies, Alzheimer's, infertility, anemia, muscular dystrophy, multiple sclerosis, cardiomyopathy, cirrhosis, cystic fibrosis, pancreatitis, Parkinson's disease, fibromyalgia, heart disease, scoliosis, sickle cell anemia, sudden infant death syndrome |
| Ag | impetigo, boils, infection, candida, influenza, cerebral-spinal meningitis, colitis, pneumococci, cystitis, dermatitis, diphtheria, diplococcus, staphylococci, warts, dysentery |
| S | arthritis, asthma, migraines, acne, muscle pain, back pain, nerve disorders, constipation, stress, circulatory problems, skin disorders, urinary tract disorders, inflammation |
| Sn | hair loss, hearing loss |
| V | cardiovascular disease, infertility, diabetes, metabolic dysfunction, high cholesterol, obesity, hyperinsulinism, pancreatic dysfunction, hypoglycemia |
| Zn | angina, Alzheimer's, hypertension, anemia, hair loss, infertility, alcoholism, infection, acne, anorexia, bulimia, miscarriage, birth defects, obesity, Crohn's disease, depression, thyroid disorders, diabetes, urinary tract infections |

Again, although specific exemplary illnesses are described above, it should be understood that any disease related to an imbalance (either excess or deficiency) in a particular mineral may be the subject of a specifically tailored diagnostic test.

The present invention is also directed to a method of manufacturing a diagnostic test for an elemental imbalance (either excess or deficiency) according to the above description.

Figure 3:
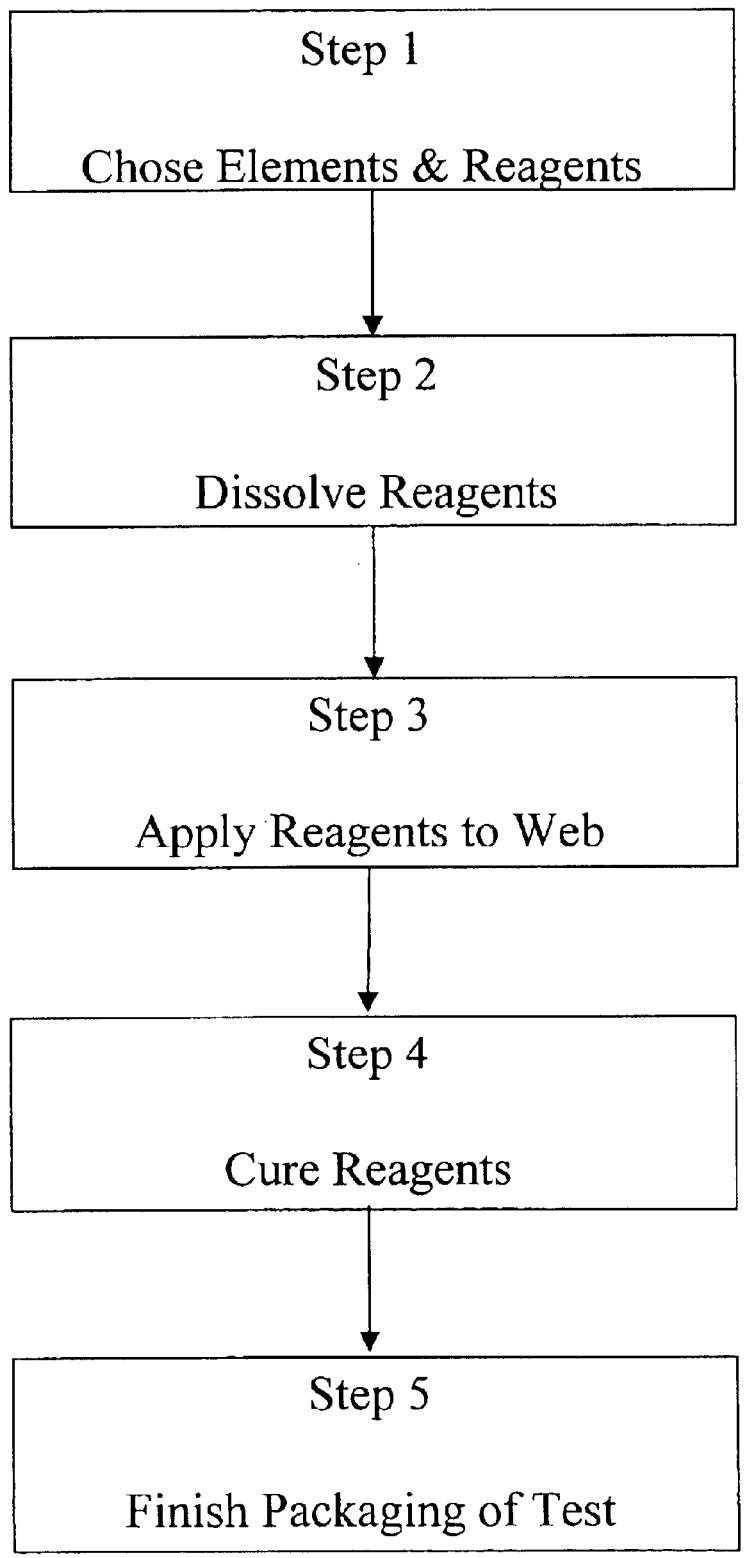
FIG. 3 is a flow chart of a method of manufacturing a diagnostic test according to the current invention.

A flow chart for one embodiment of a method of manufacturing a diagnostic test according to the current invention is provided in FIG. 3. As shown, in step 1 a group of elemental materials are chosen for testing. Once the elemental minerals of interest are determined, the corresponding reagents are chosen. Once the reagents are chosen they are put into individual solutions using appropriate solvents, for example distilled and deionized water (step 2).

In step 3, the reagent solutions are then printed on a continuous web of material, such as a tarred nylon carrier, at prescribed positions. The reagents may be laid in a quantity and width suitable for the particular test. In addition, a buffer zone may be left between each reagent on the continuous web such that cross-contamination and reaction are avoided. For example, each reagent may be printed on the web in a line having a sieve sized #80 or a mesh sized 0.177 mm in width, a gap of equal length can then be laid between each reagent to prevent cross-contamination of the reagent lines.

In step 4, the web is cured such that the reagents are recrystallized and fixed into position on the continuous web. Any curing process may be utilized in fixing the reagents onto the web, such as baking in a conventional thermal oven or via an infrared curing oven. In addition, any curing time and temperature may be utilized such that the reagents recrystallize without decomposing. In one example, an infrared oven is utilized at 105° F. for 15 minutes.

In step 5, once the reagents are deposited and cured the web is finished and packaged for sale. Such a step may include many sub-steps including: cutting the web to a suitable size and shape; attaching the web to suitable product packaging; printing any instructional or consumer warning messages onto the packaging; and boxing or wrapping the test for final shipment. For example, the finishing process in one exemplary embodiment includes: applying a bead of adhesive to the back side of the web at prescribed locations; perforated rotary die cutting the web to a specified size and shape; attaching the perforated portion of the web to a sample container; and printing instructions and scale information on the web or box and boxing the test for shipment.

Figure 4:
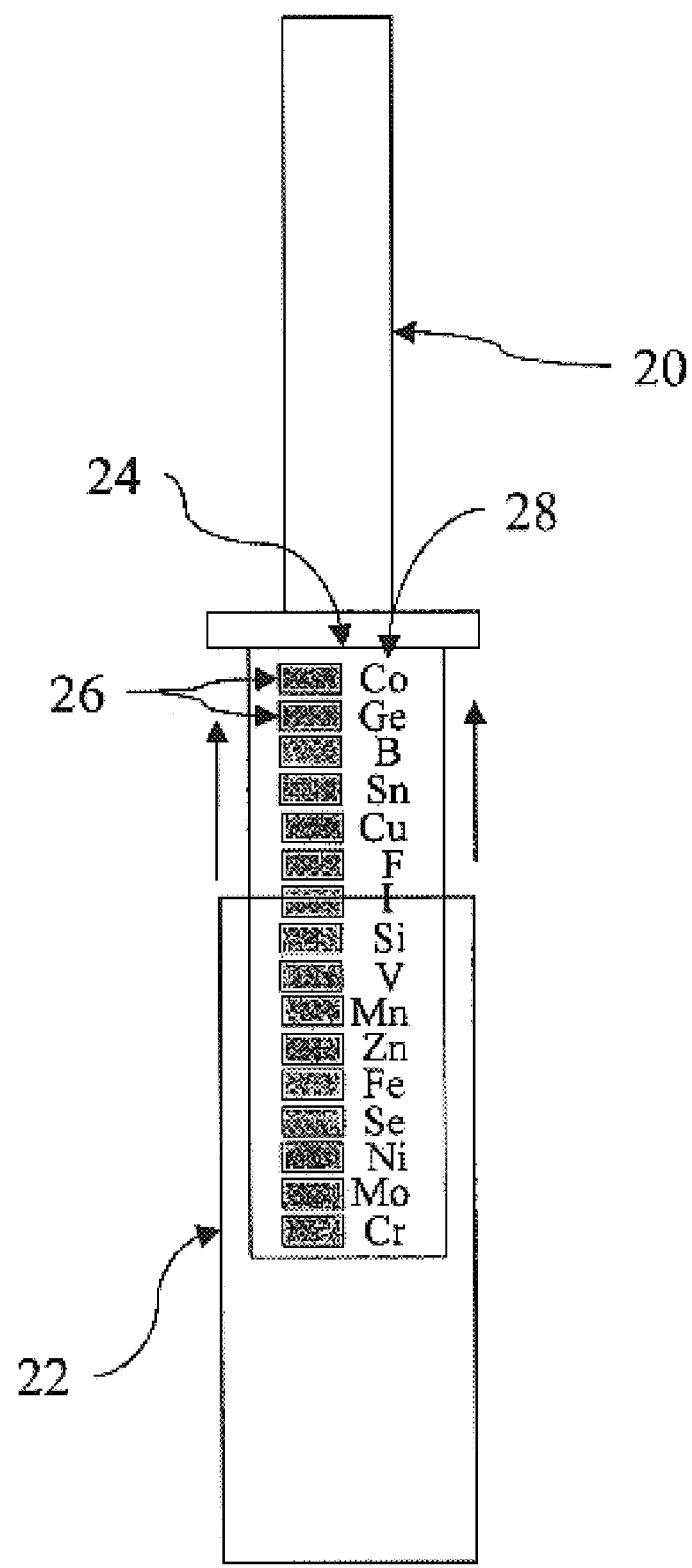
FIG. 4 is a schematic view of an exemplary embodiment of a diagnostic test according to the invention.

As described above, although the test may be made in any size and shape and of any suitable material, in one exemplary embodiment the test container is designed as an elongated dipstick 20 as shown in FIG. 4, with a biological sample collection vessel 22 attached thereto as a protective top. The web 24 containing the reagents 26 is affixed to the dipstick such that the user can collect the biological sample in the container and place the dipstick into the container in a sealing configuration. Once the reagents are in contact with the urine, the user can wait a suitable period of time and, if the test is a colorimetric or other visual-based test, the results may be instantly read by the user. If any of the reagents react, the user can then either directly read the identity of the mineral imbalance, or, if the scale 28 is printed separately, for example on a box-top sleeve, the dipstick may be placed next to or slid into the sleeve such that the reagent indicator is read against the scale.

Regardless of the actual design of the test, functionally the test should include a biological collection container, a reagent substrate designed such that the collection container can be mated thereto exposing the reagents to the biological sample, and a scale or other device to help the user interpret the reaction of the various reagents to the sample.

For example, although a dipstick design is shown in FIGS. 2 and 4 and discussed above, the reagents could be placed onto the top of the biological container itself such that simply inverting the container would expose the reagents to the sample. Alternatively, although the devices described above expose all of the reagents to the sample simultaneously, the diagnostic test could be designed such that each of the reagents is individually exposed to the sample, such as through a dropper, or via individual fluidic channels.

Finally, it should be understood that although this test is designed to provide a method of allowing self-diagnosis of an elemental imbalance by a user, the diagnostic test is not designed to provide quantitative information about the imbalance. It would be expected, and should be provided in the instructions of the test, that a user finding a positive indication of an elemental imbalance immediately contact a physician for a detailed quantitative analysis of the particular elemental imbalance found by the screening test of the current invention. Accordingly, it should be understood that while the test is designed for home use, it could also be utilized in a hospital setting as a screening test in combination with a more quantitative test available from a hospital laboratory. In one exemplary embodiment, the packaging of the home diagnostic test may include a list of the quantitative test codes or diagnostic codes suggested by the federal government, or a particular hospital or insurance provider given a particular diagnosis indication by the diagnostic test of the present invention.

Although specific embodiments are disclosed herein, it is expected that persons skilled in the art can and will design alternative diagnostic tests and methods to produce the diagnostic tests that are within the scope of the following claims either literally or under the Doctrine of Equivalents.

What is claimed is:

1. A self-diagnostic test for detecting a mineral imbalance in a user comprising:

a plurality of mineral specific reagents, each mineral specific reagent being selected to react with a different selected mineral within a biological sample such that when the selected mineral specific reagent is exposed to a concentration of the selected mineral in the biological sample outside a concentration range indicative of a standard concentration level for an individual, a visible change is induced in the selected mineral specific reagent; and a diagnostic guide for comparing the visible changes of the plurality of reagents against at least one standard for the visible changes indicative of the presence of a selected mineral imbalance disorder.

2. The self-diagnostic test as described in claim 1 wherein the plurality of mineral specific reagents are selected to detect at least one mineral from a mineral family selected from the group consisting of microtrace, trade, and all naturally occurring.

3. The self-diagnostic test as described in claim 1 wherein the plurality of mineral specific reagents are selected to detect at least one mineral that does not occur naturally within the human body.

4. The self-diagnostic test as described in claim 1 wherein the plurality of mineral specific reagents are selected to detect a mineral imbalance indicative of a disorder selected from the group consisting of ADD/ADHD, Alzheimer's disease, anemia, ataxia, bipolar disorder, birth defects, blood disorders, brain damage, brain disease, breast cancer, breathing disorders, bone cancer, cardiomyopathy, general cancer, Crohn's disease, depressive disorders, encephalopathy, eye damage, heart damage, high blood pressure, infertility, intestinal disorders, leishmaniasis, liver cancer, liver damage, lung damage, lung disease, lung cancer, kidney damage, kidney disease, manic disorders, nerve damage, neuropathy, organ damage, pancreatic cancer, periodontal disease, psychosis, renal failure, skin disorders, and Wilson's disease.

5. The self-diagnostic test as described in claim 1 wherein the plurality of mineral specific reagents are selected to detect an imbalance in a plurality of minerals selected from the group consisting of B, Ge, F, I, Si, V, Cr, Co, Cu, Fe, Ni, Mo, Se, Zn, Sn, and Mn.

6. The self-diagnostic test as described in claim 5 wherein the mineral specific reagents are selected from the group consisting of azomethine-H; chromotropic acid; dinitronaphthalenediol; 3,5-di-t-butylcatechol; 2,6-dihydroxybenzoic acid; curcumin; 5-Br-PAPS; nitrophenylfluorone; diphenylcarbazide; 5-Br-PADAP; BTAMB; TAMSMB; 5-Cl-PADAB; dithizone; 3,5-diBr-PAMB; nitroso-DMAP; nitroso-PSAP; nitroso-DEAP; 5-Br-PADAB; bathocuproin disulfonic acid disodium salt; bathocuproin; 3,5-diBr-PAESA; sodium bicinchoninate; neocuproin; 5-Br-PSAA; TMPyP; Na-DDTC; alfusone; chromazurol S; phenylfluorone; $K_2HgI_4/I_2$; bindschedler's green leuco base; diphenylcarbazone; tris(1,10-phenanthroline)Fe(II) complex; bathophenanthroline disulfonic acid disodium salt; TPTZ; PDTS; PDT; nitro-PAPS; PPKO; ferrene S; PAR; oxine; DDTC; toluene-3,4-dithiol; PAN; dimethylglyoxime; bismuthiol-2; 2,3-diaminonaphthalene; PV; SATP; toluene-3,4-dithiol; henylfluorone 3,3-diaminobenzidine; o-phenylenediamine; 4-chloro-o-phenylenediamine; ammonium molybdate; malachite green; BPA; zincon; XO; TMPyP; zinquin ethyl ester; and T(5-St)P.

7. The self-diagnostic test as described in claim 1 wherein the plurality of mineral specific reagents are selected to detect an imbalance in a plurality of minerals selected from the group consisting of Ca, Cl, Mg, P, Na, and S.

8. The self-diagnostic test as described in claim 7 wherein the mineral specific reagents are selected from the group consisting of PC; MX; indo 1; indo 1-AM; chlorophosphonazo-III; neo-thorin; fluo 3; fluo 3-AM; arsenazo-III; HDOPP-Ca; rhod 2; rhod 2-AM; GHA; quin 2; quin 2-AM; calmagite; fura 2; fura 2-AM; thio-michler's ketone; MQAE; SPQ; diethylcarbamate-Cu; diphenylcarbazone; triocytlin; tris (1,10-phenanthroline)Fe(II); Co(3)-5-Cl-PADAP; malachite green; bis(12-crown-4); nitrophenylazo-15-crown-5; oxine; pararosaniline; barium chloranilate; methylene blue; 0-phthalaldehyde; p-phenylenediamine; tris[2-(phenyliminomethyl) pyridinato]iron; and 2-aminoperimidine HCl/HBr.

9. The self-diagnostic test as described in claim 1 wherein the plurality of mineral specific reagents are selected to detect an imbalance in a plurality of minerals selected from the group consisting of Li, Be, Ne, Al, Sc, Ti, Ga, As, Br, Kr, Rh, Sr, Y, Zr, Nb, Tc, Ru, Rh, Pd, Ag, Cd, In, Sb, Te, Xe, Cs, Ba, La, Hf, Ta, W, Re, Os, Ir, Pt, Au, Hg, Tl, Pb, Bi, Po, At, Rn, Fr, Ra, Ac, Ce, Pr, Nd, Pm, Sm, Eu, Gd, Tb, Dy, Ho, Er, Yb, Lu, Th, Pa and U.

10. The self-diagnostic test as described in claim 9 wherein the mineral specific reagents are selected from the group consisting of lumogallion; o,o'-dihydroxyazobenzene; aluminon; oxine; 5Br-PADAP; rhodamine B; brilliant green; arsemate; thionalide; nitrocatechol; ethyl violet; dimethylsulfonazo-III; sulfonazo-III; chlorophosphonazo-III; chromazural S; arsenazo-I; acetylacetone; beryllon-III; 2-methyloxine; bismuthio-II; XO; DDTC; dithizone; bindschedler's green leuco base; diphenylcarbazone; PAN; formaldoxime; pyrogallol red-AM; cesibor tetraphenylborate; $EuAc_3$ $Eu_2O_3$; $GdAc_3$; $Gd(NO_3)_2$; sincon; semiethylxylenol Blue; $KAu(CN)_2$; $NaAuCl_4$; $KAuCl_4$; $KAuI_4$; 5-(p-dimethylaminobenzylidene) rhodamine; PAR; $K_3IrCl_6$; $Na_3IrCl_6$; $SnCl_2$-HBr; leuco-crystal violet; $PbAc_2$; $PbCl_2$; $Pb(NO_3)_2$; MePbAc; TPPS; thorin; bibenzyl-14-crown-4; phosphododecyl-14-crown4; TTD-14-crown-4; methyldodecyl-12-crown-4; dibenzothiazolylmethane; EtHg$Cl_2$; EtHgphosphate; Hg $(CN)_2$; EtHgthiosalicylate (thiomersal); mersalyl; PCMB; PHMB; PCMBS; PhEgAc; $HgCl_2$; $HgAc_2$; $HgSO_4$; mercurochrome; Baker's reagent (2Hg); tetrakismercuryacetate (TAM)(4Hg); STTA; thio-Michler's ketone; di-alpha-napthaylthiocarbonate; sulfochlorophenol-S; TPAC; BPR; phenylfluorone; $Os(NH_3)_6I_3$; $K_2OsCl_6$; $K_2OsO_4$; tiron; $K_2PdCl_4$; $K_2PdBr_4$; $K_2PdI_4$; $PdCl_2$; $Pd(NO_3)_2$; BTAMB; 5-Br-PSAA; 5-Br-PAPS; thiooxine; p-nitroso-N,N'dimethylaniline; $K_2PtCl_4$; $K_2PtCl_6$; $K_2PtI_6$; $K_2Pt(NO_2)_4$; $Pt(NH3)_2Cl_2$; Pt(ethylenediamine)$Cl_1$; $K_2Pt(CN)_4$; $ReCl_3$; 2-furildioxime; dimethylglyoxime; methylene blue; kalibor; TPTZ; 1,10-phenanthroline; $SmAc_3$; $Sm(NO_3)_3$; $SmCl_4$; 5,7-dichlorooxine; quinizarin; $AgNO_3$; $KAgCN_2$; 3,5-diBr-PADAP; 3,5-diBr-PAESA; 2-amino-6-methylthio-4-pyrimidine-carboxylic acid; PC; dinitrosulfonazo-III; murexide; bismuthiol-2; diethydithiocarbamate; malachite green; $Th(NO_3)_4$; arsenazo-III; morin; diantipyrylmethane; 0,0'-dihydroxyazobenzene; crystal violet; alizarin; $Na_2WO_4$; toluene-3,4-dithiol; $UO_2Ac_2$; $K_3UO_2F_5$; $UO_2(NO_3)_2$; $UO_2SO_4$; $TbCl_3$; $YbAc_3$; $Zr(NO_3)_4$; PV; TAN; and alizarin red S.

11. The self-diagnostic test as described in claim 1 wherein the plurality of mineral specific reagents are selected to detect an imbalance in a plurality of minerals selected from the group consisting of Np, Pu, Am, Cm, Bk, Cf. Es, Fm, Md, No, La, Rf, Db, Sg, and Bh.

12. The self-diagnostic test as described in claim 1 wherein the biological sample is selected from the group consisting blood, urine, saliva, mucous, and tears.

13. The self-diagnostic test as described in claim 1 wherein the visual change is a colorimetric change.

14. A self-diagnostic test apparatus comprising:
a body having at least one biological fluid receptacle disposed thereon;
a biological sample conduit in fluid communication with the at least one biological fluid receptacle; and
a plurality of mineral specific reagents disposed such that each mineral specific reagent may be exposed to a biological sample deposited within the at least one biological fluid receptacle, the mineral specific reagents being selected to react with a different selected mineral within the biological sample such that when the selected mineral specific reagent is exposed to a concentration of the selected mineral in the biological sample outside a concentration range indicative of a standard concentration level for an individual, a visible change is induced in the selected mineral specific reagent; and
a diagnostic guide for comparing the visible changes of the plurality of reagents against at least one standard for the visible changes indicative of the presence of a selected mineral imbalance disorder.

15. The self-diagnostic test apparatus as described in claim 14 comprising a plurality of biological fluid receptacles wherein each of the plurality of mineral specific reagents is independently disposed within a different one of the plurality of biological fluid receptacles.

16. The self-diagnostic test apparatus as described in claim 14 wherein each of the plurality of mineral specific reagents is disposed on a different at least one substrate removably disposed within the at least one biological fluid receptacle.

17. The self-diagnostic test apparatus as described in claim 16 wherein each of the different at least one substrates is a dipstick.

18. The self-diagnostic test apparatus as described in claim 14 wherein at least a portion of the body is transparent such that the visible change of the selected mineral specific reagents may be externally viewed.

19. The self-diagnostic test apparatus as described in claim 14 wherein the plurality of mineral specific reagents are selected to detect at least one mineral from a mineral family selected from the group consisting of microtrace, trace, and all naturally occurring.

20. The self-diagnostic test apparatus as described in claim 14 wherein the plurality of mineral specific reagents are selected to detect at least one mineral that does not occur naturally within the human body.

21. The self-diagnostic test apparatus as described in claim 14 wherein the plurality of mineral specific reagents are selected to detect a mineral imbalance indicative of a disorder selected from the group consisting of ADD/ADHD, Alzheimer's disease, anemia, ataxia, bipolar disorder, birth defects, blood disorders, brain damage, brain disease, breast cancer, breathing disorders, bone cancer, cardiomyopathy, general cancer, Crohn's disease, depressive disorders, encephalopathy, eye damage, heart damage, high blood pressure, infertility, intestinal disorders, leishmaniasis, liver cancer, liver damage, lung damage, lung disease, lung cancer, kidney damage, kidney disease, manic disorders, nerve damage, neuropathy, organ damage, pancreatic cancer, periodontal disease, psychosis, renal failure, skin disorders, and Wilson's disease.

22. The self-diagnostic test apparatus as described in claim 14 wherein the plurality of mineral specific reagents are selected to detect an imbalance in a plurality of minerals selected from the group consisting of B, Ge, F, I, Si, V, Cr, Co, Cu, Fe, Ni, Mo, Se, Zn, Sn, and Mn.

23. The self-diagnostic test apparatus as described in claim 14 wherein the biological sample is selected from the group consisting blood, urine, saliva, mucous, and tears.

24. The self-diagnostic test apparatus as described in claim 14 wherein the visual change is a colorimetric change.

25. A method of manufacturing a self-diagnostic test comprising the steps of: providing a body having at least one biological fluid receptacle disposed thereon;
providing a biological sample conduit;
connecting the biological sample conduit with the at least one biological fluid receptacle to provide a fluid connection therebetween; and
depositing a plurality of mineral specific reagents within the body such that each mineral specific reagent may be exposed to a biological sample deposited within the at least one biological fluid receptacle, the mineral specific reagents being selected to react with a different selected mineral within the biological sample such that when the selected mineral specific reagent is exposed to a concentration of the selected mineral in the biological sample outside a concentration range indicative of a standard concentration level for an individual, a visible change is induced in the selected mineral specific reagent; and
providing with said body a diagnostic guide for comparing the visible changes of the plurality of reagents against at least one standard for the visible changes indicative of the presence of a selected mineral imbalance disorder.

26. The method as described in claim 25 wherein the step of depositing comprises depositing each of the plurality of mineral specific reagents independently within a different one of the plurality of biological fluid receptacles.

27. The method as described in claim 25 wherein the step of depositing comprises depositing each of the plurality of mineral specific reagents on a different at least one substrate removably disposed within the at least one biological fluid receptacle.

28. A method of diagnosing a mineral imbalance comprising the steps of:
providing a plurality of mineral specific reagents, each mineral specific reagent being selected to react with a different selected mineral within a biological sample such that when the selected mineral specific reagent is exposed to a concentration of the selected mineral in the biological sample outside a concentration range indicative of a standard contration level for an individual, a visible change is induced in the selected mineral specific reagent;
obtaining a biological sample from a patient;
exposing the plurality of mineral specific reagents to the biological sample; and
comparing the visible changes of the plurality of mineral specific reagents against a diagnostic guide having at least one standard for visible changes indicative of the presence of a selected mineral imbalance disorder.

29. The method as described in claim 28 wherein the plurality of mineral specific reagents are selected to detect a mineral imbalance indicative of a disorder selected from the group consisting of ADD/ADHD, Alzheimer's disease, anemia, ataxia, bipolar disorder, birth defects, blood disorders, brain damage, brain disease, breast cancer, breathing disorders, bone cancer, cardiomyopathy, general cancer, Crohn's disease, depressive disorders, encephalopathy, eye damage, heart damage, high blood pressure, infertility, intestinal disorders, leishmaniasis, liver cancer, liver damage, lung damage, lung disease, lung cancer, kidney damage, kidney disease, manic disorders, nerve damage, neuropathy, organ damage, pancreatic cancer, periodontal disease, psychosis, renal failure, skin disorders, and Wilson's disease.

30. The method as described in claim 28 wherein the biological sample is selected from the group consisting blood, urine, saliva, mucous, and tears.

31. The method as described in claim 28 wherein the visual change is a colorimetric change.

* * * * *

UNITED STATES PATENT AND TRADEMARK OFFICE
CERTIFICATE OF CORRECTION

PATENT NO.     : 6,821,786 B2
DATED          : November 23, 2004
INVENTOR(S)    : Rupp It is certified that error appears in the above-identified patent and that said Letters Patent is hereby corrected as shown below:

Title page
Item [56], References Cited, OTHER PUBLICATIONS,
Jackson, M.J. "Diagnosis and detection.." reference, delete "mineral", insert
-- minerals --.
Subramanian, K. S., et al., "Detection of trace..." reference, delete "(1995", insert
-- (1995) --.
"Cu++"; Proceedings of the Neurological..." reference, delete "(NAWD", insert
-- (NAWD) --.
Giorgio; Anthony J., et al.; "Determination of..." reference, delete "Dibezyl", insert
-- Dibenzyl --.
Hauser, Russ, et al..; "Urine Vanadium..." reference, delete "Concentration sin", insert
-- Concentrations in --.

Column 11,
Line 23, delete "trade", insert -- trace --.
Lines 53-54, delete "nitrophenylfluorone", insert -- o-nitrophenylfluorone --.

Column 12,
Line 13, delete "thio-michler's", insert -- thio-Michler's --.
Line 32, delete "5Br-PADAP", insert -- 5-Br-PADAP --.
Line 44, delete "phosphododecyl-l4-crown4", insert -- phosphododecyl-14-crown-4 --.
Line 46, delete "Hg $(CN)_2$", insert -- $Hg(CN)_2$ --.
Line 47, delete "PhEgAc", insert -- PhHgAc --.
Line 50, delete "di-alpha-napthaylthiocarbonate", insert
-- di-alpha-naphthylthiocarbonate --.
Line 55, delete "Pt(NH3)$_2$Cl$_2$", insert -- $Pt(NH_3)_2Cl_2$ --.
Line 56, delete "Pt(ethylenediamine)Cl$_1$", insert -- $Pt(ethylenediamine)Cl_2$ --.
Line 62, delete "diethydithiocarbamate", insert -- diethyldithiocarbamate --.

Column 13,
Line 8, after "consisting", insert -- of --.

Column 14,
Line 13, after "consisting", insert -- of --.
Line 17, delete "of: providing", insert -- of:
                                            providing --.
Line 57, delete "contration", insert -- concentration --.

UNITED STATES PATENT AND TRADEMARK OFFICE
CERTIFICATE OF CORRECTION

PATENT NO. : 6,821,786 B2
DATED : November 23, 2004
INVENTOR(S) : Rupp

It is certified that error appears in the above-identified patent and that said Letters Patent is hereby corrected as shown below:

Column 16,
Line 6, after "consisting", insert -- of --.

Signed and Sealed this

Seventh Day of February, 2006

JON W. DUDAS
*Director of the United States Patent and Trademark Office*